United States Patent [19]
Bauer et al.

[11] Patent Number: 5,847,197
[45] Date of Patent: Dec. 8, 1998

[54] PROCESS FOR THE PREPARATION OF AMINOMALONIC ACID ESTER SALTS

[75] Inventors: Frank Bauer; Marcel Feld, both of Cologne, Germany

[73] Assignee: Huels Aktiengesellschaft, Marl, Germany

[21] Appl. No.: 868,799

[22] Filed: Jun. 4, 1997

[30] Foreign Application Priority Data

Jun. 4, 1996 [DE] Germany .......................... 196 22 325.3

[51] Int. Cl.⁶ ................................................. C07C 229/00
[52] U.S. Cl. ............................ 560/171; 560/38; 560/125; 560/145
[58] Field of Search ..................................... 560/171, 125, 560/38, 145

[56] References Cited

U.S. PATENT DOCUMENTS 2,521,809  9/1950  Tishler ..................................... 560/171
3,941,823  3/1976  Hashimoto ............................... 560/171

*Primary Examiner*—Michael L. Shippen
*Attorney, Agent, or Firm*—Oblon, Spivak, McClelland, Maier & Neustadt, P.C.

[57] ABSTRACT

The invention relates to a process for the preparation of aminomalonic acid esters and optionally their salts by the catalytic hydrogenation of a substituted malonic acid ester in an inert solvent, and optionally by the addition of an acid to the hydrogenation mixture. The process comprises carrying out the hydrogenation in the presence of a solid dehydrating agent and a solvent or solvent mixture in which the aminomalonic acid ester salt is substantially insoluble.

10 Claims, No Drawings

PROCESS FOR THE PREPARATION OF AMINOMALONIC ACID ESTER SALTS

BACKGROUND OF THE INVENTION

1. Field of the Invention

The invention relates to an improved process for the preparation of aminomalonic acid esters by catalytic hydrogenation of the corresponding nitro, nitroso or optionally O-substituted hydroxyimino compounds. The aminomalonic acid esters can be converted to the aminomalonic acid ester salts by neutralization with an acid.

2. Description of the Related Art

Aminomalonic acid esters and their salts, wherein these compounds contain ammonium groups, are valuable structural units for the synthesis of heterocycles. A number of processes for the preparation of aminomalonic acid esters have been disclosed in which the corresponding nitro, nitroso or optionally O-substituted hydroxyimino compounds are reduced. Thus, Gabriel et al. (B. 27 [1894], 1141) describe reduction by means of tin, tin(II) chloride and hydrochloric acid. According to Cherchez (Bull. Soc. Chim. Fr.(4)47 [1930], 1282) and Lindemann et al. (Chem. Ber. 63 [1930], 710), an aluminum amalgam can be used as the reducing agent. Siya et al. (Syntheses 1986, 133) reduce the starting materials with ammonium formate. According to FR-1.171.906, aminomalonic acid esters also can be prepared electrochemically by cathodic reduction.

These processes predominantly employ expensive reducing agents. They additionally produce large amounts of salts which are difficult to dispose of. The electrochemical process is only suitable on the industrial scale for manufacturers who are equipped for electrochemistry.

Wesseley et al. (Monatsh. Chem. 83 [1952], 678, 687) describe the reduction of starting materials by catalytic hydrogenation with catalysts like Raney nickel, palladium on activated charcoal and platinum on activated charcoal. Selective hydrogenation to give carboxylic acid ester groups is successful because their conversion to methylol groups requires much more vigorous conditions than hydrogenation of A the nitro, nitroso or hydroxyimino groups to amino groups. Such conditions, i.e. temperatures well above 100° C. for example, are not recommended because aminomalonic acid esters are sensitive molecules which tend to undergo intermolecular condensation reactions. For this reason, it is advisable to obtain the aminomalonic acid esters in the form of their salts if they are not to be immediately reacted further in the reaction mixture.

The catalytic hydrogenation of nitro-, nitroso- and hydroxyimino-malonic acid esters has always been carried out in an inert solvent. A desirable solvent is one in which the aminomalonic acid ester salt is insoluble or as sparingly soluble as possible. However, if such a solvent is used, e.g. toluene, methyl acetate, ethyl acetate or methyl tert-butyl ether, the hydrogenation proceeds very slowly and incompletely. Although this can be counteracted by working in high dilution, the resulting space-time yields are unacceptable on an industrial scale.

Both satisfactory reaction rates and good space-time yields can be achieved with ethanol as the solvent. The aminomalonic acid ester salts are readily soluble in ethanol, however, so they cannot be separated off by precipitation. The process, as reported in Org. Synth. 40, 24, attempts to resolve the dilemma that some solvents are suitable for the hydrogenation stage but unsuitable for separation of the salt, whereas other solvents exhibit the converse behavior. In this process, the hydrogenation is carried out in ethanol, the solvent is distilled off at a maximum of 50° C., the residue is taken up with diethyl ether and the aminomalonic acid ester hydrochloride is precipitated out by the introduction of hydrogen chloride gas. However, this process is more expensive than the desired procedure, where the same solvent is used in the hydrogenation and precipitation stages.

Also, especially on an industrial scale, it incurs increased product losses as a result of the abovementioned tendency of aminomalonic acid esters to undergo condensation reactions. According to the reverse of the dilution principle, this tendency naturally becomes more pronounced as the ethanol is distilled off and the concentration of the aminomalonic acid ester increases until it is ultimately in solvent-free form.

These product losses due to condensation reactions are extensively avoided if firstly the hydrogenation is carried out in ethanol and then a non-polar solvent, such as toluene, is added to the hydrogenation mixture before precipitation of the salt. However, the yield of aminomalonic acid ester salt is then unsatisfactory because it is very soluble in the solvent mixture. Moreover, after the salt has been filtered off, this solvent mixture is not reusable without working up.

SUMMARY OF THE INVENTION

It has now been found, surprisingly, that aminomalonic acid esters of the general formula I:

in which R' and R" can be identical or different and are alkyl, cycloalkyl, aryl, alkaryl or aralkyl radicals and R is defined in the same way as R' and R" and can additionally be hydrogen, and optionally their salts of the general formula II:

in which R', R" and R are as defined for the formula I, Y is an acid anion and n is the basicity of the acid $H_nY$, can be advantageously prepared by the catalytic hydrogenation of a substituted malonic acid ester of the general formula III:

in which R', R" and R are as defined for the formula I and X is a nitro, nitroso or optionally O-substituted hydroxyimino group, in an inert solvent, and optionally by the addition of an acid of the formula $H_nY$, in which Y and n are as defined for the formula II, if the hydrogenation is carried out in the presence of a solid dehydrating agent and a solvent or solvent mixture in which the aminomalonic acid ester salt II is substantially insoluble.

The hydrogenation stage of the process according to the invention produces the aminomalonic acid esters I with high yields in a rapid reaction and hence with high space-time yields, even when using solvents which, in contrast to ethanol, do not contain hydroxyl groups. The latter variant is advantageous if it is planned immediately to react the aminomalonic acid ester I further in the reaction mixture with reactants which contain substituents sensitive to alcoholysis. In the neutralization stage, the aminomalonic acid ester salts II are obtained in high purity and, based on the aminomalonic acid esters I from the hydrogenation stage, in practically quantitative yield. The same solvents are used in both stages of the process. These can be solvent mixtures, although they do not then have to be worked up but, like single solvents, can be used as such for a new batch.

In the substituted malonic acid esters III preferred as starting materials, and correspondingly also in the preferred aminomalonic acid esters I and their salts II, R' and R" are identical alkyl radicals having 1 to 4 carbon atoms and R is preferably hydrogen or a hydrocarbon radical having 1 to 8 carbon atoms, especially an alkyl radical having 1 to 4 carbon atoms. In the preferred substituted malonic acid esters III, X is the nitro group or the hydroxyimino group, which can be O-substituted by a hydrocarbon radical having 1 to 8 carbon atoms, especially an alkyl radical having 1 to 4 carbon atoms, or an acyl radical having 2 to 8 carbon atoms. The substituted malonic acid esters III can be used individually or in a mixture.

Examples of suitable substituted malonic acid esters III are dimethyl nitromalonate, diethyl nitromalonate, dibenzyl nitromalonate, dimethyl methylnitromalonate, dimethyl methylnitrosomalonate, diethyl isobutylnitrosomalonate, diethyl hydroxyiminomalonate, dimethyl O-acetylhydroxyiminomalonate, diethyl O-benzoylhydroxyiminomalonate, diethyl O-methylhydroxyiminomalonate, diisopropyl O-phenylhydroxyiminomalonate, di-n-butyl O-n-butylhydroxyiminomalonate, dimethyl O-n-octylhydroxyiminomalonate, diethyl methylnitromalonate, diethyl O-acetylhydroxyiminomalonate, dimethyl hydroxyiminomalonate, diisopropyl hydroxyiminomalonate, etc.

DETAILED DESCRIPTION OF THE PREFERRED EMBODIMENTS

The first stage of the process is a catalytic hydrogenation, the catalysts used being those which are known to be suitable for the hydrogenation of nitro, nitroso and optionally O-substituted hydroxyimino groups to amino groups, such as platinum, palladium, rhodium and nickel catalysts. The catalytically active metals can be present as such or applied to a support. Examples which may be mentioned are Raney nickel, palladium black, palladium on activated charcoal, platinum black, platinum on activated charcoal, palladium/platinum on aluminum oxide, silicon dioxide, calcium carbonate or barium sulfate, and platinum oxide. The amount of catalyst is not critical and can be easily determined by means of preliminary experiments. Noble metal catalysts are generally used in amounts of 0.0001 to 0.05 part by weight of metal per part by weight of substituted malonic acid ester III.

An important feature of the invention is the concomitant use of a solid dehydrating agent in the hydrogenation stage. Any known solid dehydrating agents which are capable of binding the water formed in the hydrogenation reaction at the appropriate reaction temperature, e.g. as water of crystallization, are suitable for this purpose. Suitable solid dehydrating agents are predominantly of an inorganic nature and have a reversible action, i.e. they can be regenerated by heating once they are completely laden with water. Examples of suitable dehydrating agents are calcium chloride, sodium sulfate, magnesium sulfate, sodium acetate, sodium carbonate, potassium carbonate, calcium sulfate, aluminum oxide, silica gels, dry synthetic resin ion exchangers, copper(II) sulfate, montmorillonite, calcium oxide, barium oxide and magnesium oxide. The natural or synthetic zeolites known as molecular sieves are also outstandingly suitable for the process according to the invention.

The amount of solid dehydrating agent must be chosen so as to prevent an aqueous phase from separating out in the reaction mixture. The minimum amount depends on the substituted malonic acid ester III in question (e.g. nitro compounds give twice as much water as hydroxyimino compounds), the water absorbing capacity of the chosen dehydrating agent and the water solubilizing capacity of the solvent or solvent mixture at the reaction temperature. However, it is also possible to use larger amounts of dehydrating agent. In the case of a batch procedure, the only limitation is that it must remain possible to mix the hydrogenation mixture thoroughly. Nevertheless, excessive amounts of dehydrating agent complicate the working up, which requires a solid-liquid separation. The hydrogenation mixtures generally become difficult to handle when their content of solid dehydrating agent exceeds 50 percent by weight. It has been found in practice that it is convenient to use at least 0.02 part by weight of solid dehydrating agent per part by weight of substituted malonic acid ester III. The solid dehydrating agent is advantageously used in amounts of 0.02 to 4.0 parts by weight, especially of 0.05 to 0.25 part by weight, per part by weight of substituted malonic acid ester III. The optimal amount of solid dehydrating agent can be easily determined by means of preliminary experiments.

In the case of a continuous procedure with hydrogenation catalyst and solid dehydrating agent fixed in the form of a column, as described below, the dehydrating agent becomes progressively laden with water and the exhaustion of the dehydrating agent becomes apparent when water separates out of the product stream and when unconverted substituted malonic acid ester III can be detected. The water absorbing capacity of the solid dehydrating agent is optimally utilized in this way.

Another important feature of the process according to the invention is the use of a solvent or solvent mixture in which the aminomalonic acid ester salt II is extensively insoluble. This condition is satisfied by non-polar or weakly polar organic solvents which are substantially immiscible with water or only miscible to a limited extent. These include carboxylic acid esters, especially esters of $C_2$–$C_4$ carboxylic acids with $C_1$–$C_4$ alkanols, aliphatic and aromatic hydrocarbons which are liquid at the reaction temperature, halogenated and especially chlorinated aliphatic or aromatic hydrocarbons, monohydric alcohols having 4 to 12 carbon atoms, aromatic and aliphatic mononitriles having 2 to 13 carbon atoms and dialkyl ethers having 4 to 8 carbon atoms. Examples of suitable solvents of this type, which can be used on their own or in a mixture with one another, are n-heptane and n-octane and their isomers, benzene, toluene, ethylbenzene, 1,2-dichloroethane, n-octanol, n-dodecanol, 2-ethylhexan-1-ol, benzonitrile, caprylonitrile, xylene, diethyl ether, diisopropyl ether, methyl tert-butyl ether and acetonitrile. Particularly preferred solvents are methyl acetate and ethyl acetate.

It has proved useful in practice if the solvent or solvent mixture is capable of dissolving a small amount of water, i.e. up to about 20 percent by weight at room temperature. If a solvent has been chosen which dissolves practically no water, such as n-heptane or toluene, a hydrophilic compound miscible therewith can be added in an amount such that the solubility of water in the mixture comes within the range given. Solvents or solvent mixtures with a greater water solubilizing capacity should be avoided, at least when the aminomalonic acid ester salt is to be precipitated out; otherwise its solubility increases appreciably.

The process according to the invention can be carried out continuously or batchwise. In the case of a batch procedure, it is possible to place the solution of the substituted malonic acid ester III, the hydrogenation catalyst and the dehydrating agent in a pressure reactor, heat the mixture to the reaction temperature and introduce hydrogen under pressure until the pressure remains constant. It is convenient to ensure that the reaction mixture is thoroughly mixed. To achieve an acceptable reaction rate, the process is generally carried out, depending on the catalyst, at 0° to 100° C. and under a hydrogen pressure of 1 to 150 bar (abs.). Preferred hydrogenation temperatures are 0° to 50° C., especially 20° to 40° C. The solid components in the reaction mixture, i.e. catalyst and dehydrating agent, are separated from the liquid phase by means of a conventional solid-liquid separation, e.g. by gravity filtration or suction filtration. The yield is improved by washing the separated solid components with the solvent used. The aminomalonic acid ester is dissolved in the liquid phase and, if desired, can be reacted further therein or precipitated out as a salt. This can be done by introducing the acid $H_nY$ into the solution (conveniently cooled to room temperature in order to maximize precipitation) and separating the precipitated aminomalonic acid ester salt II from the solvent, again in conventional manner. The solvent can be used for a new batch without further treatment. This can be repeated several times until impurities, e.g. by-products, become so concentrated as to affect the yield and/or purity of the aminomalonic acid ester salt II. In this case, the solvent (solvent mixture) can be worked up by distillation.

The acid $H_nY$ can be a monobasic or polybasic, advantageously up to tribasic, organic or inorganic acid. Suitable acids include hydrogen chloride, hydrogen bromide, sulfuric acid, phosphoric acid, acetic acid, oxalic acid, methanesulfonic acid and p-toluenesulfonic acid. As appropriate, the acids can be added to the solution in gaseous form, in undiluted liquid or solid form or dissolved in a solvent (conveniently, the solvent of the hydrogenation stage).

The dehydrating agent present in the mixture with the hydrogenation catalyst can be regenerated in conventional manner, i.e. freed from the absorbed water. This can be done e.g. by heating it in an inert gas stream at 100° to 300° C., after which the mixture can be reused for a new batch. The optimal dewatering temperatures depend on the temperature at which the dehydrating agents begin to release water. Thus, in the case of salt hydrates for example, lower temperatures are usually sufficient, whereas e.g. zeolites have to be dewatered at the upper end of the temperature range. Depending on the catalyst, the heating can be carried out in an air stream or in an inert gas stream (e.g. a stream of nitrogen or argon). In another, less preferable variant, it is possible to dissolve the dehydrating agent in water, provided it is water-soluble, discard the solution and at least reuse the residual hydrogenation catalyst.

The process according to the invention can also be carried out continuously. This can be done by fixing the catalyst and the dehydrating agent, as a mixture or in layers, in a tubular reactor, heating them to the reaction temperature and then allowing the solution of the substituted malonic acid ester III to trickle over the catalyst while passing hydrogen through in cocurrent or counter-current. As far as the temperature and pressure conditions are concerned, there is no difference between the continuous procedure and the batch process described above. When the water absorbing capacity of the dehydrating agent is exhausted, water and unconverted substituted malonic acid ester III appear in the product stream. The dehydrating agent then has to be regenerated. This can be done by rinsing the catalyst and dehydrating agent with the solvent, evaporating the residual solvent by blowing warm air through the tubular reactor, and finally driving the water out of the dehydrating agent by raising the temperature accordingly and, depending on the catalyst, passing an air or inert gas stream through the tubular reactor. In another embodiment of this continuous process, two tubular reactors are arranged in parallel, the hydrogenation phase taking place in one reactor while the dehydrating agent is regenerated in the other.

If unconverted malonic acid ester III "breaks through" in the continuous process, or the hydrogenation is incomplete for any reason in the batch process, it is recommended to precipitate the aminomalonic acid ester I with an equimolar or smaller amount of acid and, after separation of the aminomalonic acid ester salt II, to recycle the filtrate into the hydrogenation stage. This procedure avoids a secondary precipitation of aminomalonic acid ester salt II during the hydrogenation, which could inactivate the catalyst.

The following Examples are given in order to illustrate the invention in greater detail and are not intended to limit the extent of protection as defined in the claims.

EXAMPLES

Example 1—Diethyl aminomalonate hydrochloride

A solution of 420.0 g of a mixture of diethyl hydroxyiminomalonate and diethyl acetoxyiminomalonate (together 2.0 mol) in 400 ml of ethyl acetate, 40.0 g of anhydrous magnesium sulfate and 12.5 g of palladium on activated charcoal (5 percent by weight of Pd) as hydrogenation catalyst were placed in a 1.5 l pressure reactor equipped with a stirrer. At 30° to 35° C., hydrogen was introduced under a pressure of 20 bar for 80 minutes until the pressure remained constant. The reactor contents were thoroughly mixed by stirring during this process. The hydrogenation mixture was cooled to 20° C. and diluted with 200 ml of ethyl acetate and the mixture of hydrous magnesium sulfate and catalyst was filtered off. The solid which had been separated off was washed three times with a total of 200 ml of ethyl acetate and the wash liquor was combined with the filtrate. Diethyl aminomalonate hydrochloride was precipitated out as a white solid by the introduction of 68 g of dry hydrogen chloride, filtered off, washed with ethyl acetate and dried under a water jet vacuum at 70° C. The yield was 359.6 g (85.1% of theory), the melting point was 165° C. and the purity according to the analytically determined chlorine content was 100%.

Example 2—Diethyl aminomalonate hydrochloride

The procedure was as in Example 1 except that the solid mixture of hydrous magnesium sulfate and catalyst obtained in this Example were washed with hot water and the catalyst recovered after drying was reused. The yield was 358.9 g (84.9% of theory), the melting point was 165° C. and the purity (according to the chlorine content) was 100%.

Example 3—Diethyl aminomalonate hydrochloride

The procedure was as in Example 1 except that the starting material was dissolved in a mixture of 400 ml of ethyl acetate and 20 ml of ethanol and the amount of magnesium sulfate was reduced to 10.0 g. The yield was 340.2 g (80.5% of theory), the melting point was 165° C. and the purity (according to the chlorine content) was 100%.

Example 4—Diethyl aminomalonate hydrochloride

The procedure was as in Example 1 except that methyl tert-butyl ether was used as the solvent. The yield was 353.1 g (83.6% of theory), the melting point was 165° C. and the yield (according to the chlorine content) was 100%.

Example 5—Dibutyl aminomalonate hydrochloride

The procedure was as in Example 1 except that 423 g of a mixture of diisobutyl hydroxyiminomalonate and diisobutyl acetoxyiminomalonate (together 1.68 mol) were hydrogenated in the presence of 400 ml of ethyl acetate and 40.0 g of anhydrous magnesium sulfate. After separation of the magnesium sulfate and catalyst, diisobutyl aminomalonate hydrochloride was precipitated by the introduction of 64.5 g of dry hydrogen chloride. The yield was 339.4 g (75.5% of theory), the melting range was 93.5°–95.5° C. and the purity (according to the chloride content) was 99%.

Example 6—Diisobutyl aminomalonate p-toluenesulfonate

The procedure was as in Example 5 except that, after separation of the magnesium sulfate and catalyst, 316.9 g of p-toluenesulfonic acid in 2688 g of ethyl acetate were added to the hydrogenation mixture and the resulting mixture was stored overnight at 5° C. The yield was 47.6 g (61.8% of theory) and the melting range was 131°–132° C.

Example 7—Diethyl aminomethylmalonate p-toluenesulfonate

A solution of 250 g of diethyl nitromethylmalonate in 450 g of ethyl acetate, 50.0 g of anhydrous magnesium sulfate and g of palladium on activated charcoal (5 percent by weight of Pd) as hydrogenation catalyst were placed in a 1.5 l pressure reactor equipped with a stirrer. At 35° to 40° C. hydrogen was introduced under a pressure of 6 to 10 bar for 50 minutes until the pressure remained constant. The reactor contents were thoroughly mixed by stirring during this process. The hydrogenation mixture was cooled to 20° C. and, after filtration of the magnesium sulfate and catalyst, a solution of 216.8 g of p-toluenesulfonic acid in 900 g of ethyl acetate was added. The solution was evaporated under a water jet vacuum to leave 383 g (93% of theory) of a light yellow oil which, according to $^{13}$C NMR analysis, consisted mainly of diethyl aminomethylmalonate p-toluenesulfonate together with p-toluenesulfonic acid and small amounts of other impurities.

Obviously, numerous modifications and variations of the present invention are possible in light of the above teachings. It is therefore to be understood that within the scope of the appended, claims, the invention may be practiced otherwise than as specifically described herein.

This application is based upon German patent application 196 22 325.3 filed Jun. 4, 1996, the entire contents of which are herein incorporated by reference.

What is claimed as new and desired to be secured by letters: patent of the United States is:

1. A process for preparing an aminomalonic acid ester of the general formula:

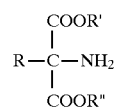

wherein R is a hydrogen, alkyl, cycloalkyl, aryl, alkaryl, or aralkyl moiety; R' is an alkyl, cycloalkyl, aryl, alkaryl, or aralkyl moiety; and R" is an alkyl, cycloalkyl, aryl, alkaryl, or aralkyl moiety, comprising the steps of:

(a) providing a reaction mixture including a hydrogenation catalyst, a solid dehydrating agent, an inert solvent, and a substituted malonic acid ester of the general formula:

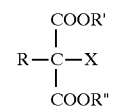

wherein R, R', and R" are defined as above; and X is a nitro, nitroso, or O-substituted hydroxyimino group; and (b) catalytically hydrogenating the substituted malonic acid ester, thereby preparing the aminomalonic acid ester.

2. The process of claim 1, wherein R, R', and R" each is an alkyl group having from 1 to 4 carbon atoms, and X is O-substituted by an alkyl group having from 1 to 4 carbon atoms.

3. The process of claim 1, wherein the dehydrating agent is selected from the group consisting of calcium chloride, sodium sulfate, magnesium sulfate, sodium acetate, sodium carbonate, potassium carbonate, aluminum oxide, a silica gel, calcium sulfate, a dry synthetic resin ion exchanger, a molecular sieve, and mixtures thereof.

4. The process of claim 3, wherein the dehydrating agent is present in an amount of from 0.02 to 4.0 parts by weight per part by weight of the substituted malonic acid ester.

5. The process of claim 4, wherein the dehydrating agent is present in an amount of from 0.05 to 0.25 parts by weight per part by weight of the substituted malonic acid ester.

6. The process of claim 1, wherein the solvent is selected from the group consisting of an alkyl acetate, an aliphatic hydrocarbon, a halogenated aliphatic hydrocarbon, an aromatic hydrocarbon, a halogenated aromatic hydrocarbon, a long-chain aliphatic alcohol, a long-chain aliphatic nitrile, a water-insoluble ether, and mixtures thereof.

7. The process of claim 1, wherein the hydrogenation step is conducted on an immobilized support containing the catalyst and the dehydrating agent by contacting the immobilized support with the substituted malonic acid ester and hydrogen.

8. The process of claim 7, further comprising after step (b) the step of extracting water from the dehydrating agent and the step of reusing the dehydrating agent for dehydration.

9. A process for preparing an aminomalonic acid ester of the general formula:

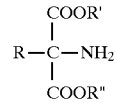

wherein R is a hydrogen, alkyl, cycloalkyl, aryl, alkaryl, or aralkyl moiety; R' is an alkyl, cycloalkyl, aryl, alkaryl, or aralkyl moiety; and R" is an alkyl, cycloalkyl, aryl, alkaryl, or aralkyl moiety, comprising the steps of:

(a) providing a first reaction mixture including a hydrogenation catalyst, a solid dehydrating agent, an inert solvent, and a substituted malonic acid ester of the general formula:

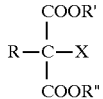

wherein R, R', and R" are defined as above; and X is a nitro, nitroso, or O-substituted hydroxyimino group;

(b) catalytically hydrogenating the substituted malonic acid ester in the first reaction mixture, thereby preparing a first quantity of the aminomalonic acid ester;

(c) removing the dehydrating agent and the catalyst from the first reaction mixture;

(d) extracting water from the dehydrating agent and the catalyst obtained in step (c);

(e) providing a second reaction mixture including an inert solvent and the substituted malonic acid ester;

(f) adding to the second reaction mixture the dehydrating agent or the catalyst obtained in step (d);

(g) catalytically hydrogenating the substituted malonic acid ester in the second reaction mixture, thereby preparing a second quantity of the aminomalonic acid ester.

10. The process of claim 9, wherein the dehydrating agent and the catalyst are removed from the first reaction mixture in step (c) by means of a solid-liquid separation technique.

* * * * *